United States Patent
Zhang et al.

(10) Patent No.: US 10,989,639 B1
(45) Date of Patent: Apr. 27, 2021

(54) EXPERIMENTAL TEST METHOD FOR SUBCRITICAL PROPAGATION RATE OF ROCK FRACTURES BASED ON TRIAXIAL STRESS—STRAIN CURVE

(71) Applicant: Chengdu University of Technology, Chengdu (CN)

(72) Inventors: Hao Zhang, Chengdu (CN); Bin Yang, Chengdu (CN); Ying Zhong, Chengdu (CN); Yang Yang, Chengdu (CN); Jiping She, Chengdu (CN); Guanchang Pan, Chengdu (CN); Kun Chang, Chengdu (CN); Xinyang Wang, Chengdu (CN)

(73) Assignee: CHENGDU UNIVERSITY OF TECHNOLOGY, Chengdu (CN)

( * ) Notice: Subject to any disclaimer, the term of this patent is extended or adjusted under 35 U.S.C. 154(b) by 0 days.

(21) Appl. No.: 17/137,388

(22) Filed: Dec. 30, 2020

(30) Foreign Application Priority Data

Dec. 31, 2019 (CN) .......................... 201911413223.X (51) Int. Cl.
*G01N 3/08* (2006.01)
*G01N 33/24* (2006.01)
*E21B 49/02* (2006.01)

(52) U.S. Cl.
CPC ............... *G01N 3/08* (2013.01); *E21B 49/02* (2013.01); *G01N 33/24* (2013.01);
(Continued)

(58) Field of Classification Search
CPC ... G01N 2203/0688; G01N 2203/0019; G01N 2203/0066; G01N 2203/0256;
(Continued)

(56) References Cited

U.S. PATENT DOCUMENTS

2014/0352949 A1* 12/2014 Amendt .................. E21B 43/26
166/250.1

FOREIGN PATENT DOCUMENTS

| CN | 105956315 A | | 9/2016 |
| CN | 108593436 A | * | 9/2018 |

OTHER PUBLICATIONS

Li et al., "Ultrasonic wave propagation characteristics for typical anisotropic failure modes of shale under uniaxial compression and real-time ultrasonic experiments", Journal of Geophysics and Engineering, vol. 17, 258-276, Dec. 18, 2019. <https://academic.oup.com/jge/article/17/2/258/5680467> (Year: 2019).*

(Continued)

*Primary Examiner* — Jonathan M Dunlap (57) ABSTRACT

The invention discloses an experimental test method for subcritical propagation rate of rock fractures based on triaxial stress-strain curve, including: Step 1: preparing test sample core for experiment; Step 2: putting core into triaxial rock mechanics test system, applying constant radial confining pressure to core, and applying axial stress in the axial direction until the core is macroscopically damaged; recording experimental parameters of axial stress, strain and corresponding loading time of the core; Step 3: drawing stress-strain curve of the test core according to detection data points of axial stress and axial strain; Step 4: in the stress-strain curve of the test core, starting time and ending time of the subcritical propagation stage of fractures inside the core correspond to the initiation stress $\sigma_{ci}$ and damage stress $\sigma_{cd}$, respectively, and calculating subcritical propagation rate of the subcritical fracture propagation stage of the test core.

4 Claims, 3 Drawing Sheets

(52) U.S. Cl.
CPC .............. *G01N 2203/0003* (2013.01); *G01N 2203/0019* (2013.01); *G01N 2203/0066* (2013.01); *G01N 2203/0067* (2013.01); *G01N 2203/0075* (2013.01); *G01N 2203/023* (2013.01); *G01N 2203/0256* (2013.01); *G01N 2203/0266* (2013.01); *G01N 2203/0676* (2013.01); *G01N 2203/0682* (2013.01); *G01N 2203/0688* (2013.01)

(58) Field of Classification Search
CPC ... G01N 2203/0266; G01N 2203/0003; G01N 2203/0682; G01N 2203/0676; G01N 2203/0075; G01N 2203/0067; G01N 2203/023; G01N 3/08; G01N 33/24; E21B 49/00; E21B 49/02
See application file for complete search history.

(56) References Cited

OTHER PUBLICATIONS

Swanson, Peter. "Subcritical crack growth and other time and environment-dependent behavior in crustal rocks", Journal of Geophysical Research, vol. 89, iss. B6, 4137-4152, Jun. 10, 1984. <https://agupubs.onlinelibrary.wiley.com/doi/abs/10.1029/JB089iB06p04137> (Year: 1984).*

Li et al., "Time-dependent dilatancy for brittle rocks", Journal of Rock Mechanics and Geotechnical Engineering 9 (2017) 1054-1070, Nov. 23, 2017. <https://www.sciencedirect.com/science/article/pii/S1674775517301191> (Year: 2017).*

Cai et al. "Generalized crack initiation and crack damage stress thresholds of brittle rock masses near underground excavations", International Journal of Rock Mechanics & Mining Sciences 41 (2004) 833-847. <https://www.sciencedirect.com/science/article/pii/S1365160904000450> (Year: 2004).*

"Evolution of Acoustic Characteristics in the Whole Stress-strain Process of Brittle Rocks" Zhang Guokai et al., Journal of Central South University (Science and Technology), vol. 50, Issue 8, pp. 1971-1980, Publication Date: Aug. 30, 2019.

* cited by examiner

EXPERIMENTAL TEST METHOD FOR SUBCRITICAL PROPAGATION RATE OF ROCK FRACTURES BASED ON TRIAXIAL STRESS—STRAIN CURVE

BACKGROUND OF THE INVENTION

Technical Field

The present invention relates to the technical field of rock mechanics research, in particular to the field of subcritical propagation mechanics of rock fracture, more specifically relating to an experimental test method for subcritical propagation rate of rock fractures based on triaxial stress-strain curve.

Description of Prior Art

To deepen the understanding of the forming mechanism of formation fractures, research on rock mechanics can effectively improve fracturing efficiency and increase oil and gas production. At present, the mainstream method is to use Griffith fracture theory, which believes that the equilibrium fracture condition of ideal brittle solid is determined by the surface energy of the solid in vacuum. However, most materials such as rocks actually fracture in environmental medium, and the environmental medium has a very significant impact on fracture process. The most obvious manifestation is that under the action of environmental medium, fractures may propagate slowly under the continuous action of load far lower than the applied critical stress. This kind of propagation is also known as subcritical fracture propagation. In oil and gas production, the subcritical fracture propagation is relatively common, the most typical of which is subcritical fracture propagation in formation rocks under the action of external fluids after the original crustal stress balance is destroyed in the drilling and completion process and the hydraulic fracturing process. It is significant to study the fracture propagation rate in subcritical propagation process for the analysis and prevention of wellbore instability during drilling and completion, and for optimization of shut-in measures after hydraulic fracturing.

The existing methods to measure the subcritical propagation rate of fractures in solid materials mainly include the double-cantilever sample method and the double-torsion sample method. As explained by Swanson et al. (Swanson P L. Subcritical fracture growth and other time- and environment-dependent behavior in crustal rocks [J]. Journal of Geophysical Research: Solid Earth, 1984, 89(B6):4137-52.), the double-cantilever beam sample method is mainly to treat the mechanical cut in the length direction of the sample, then applies the same tensile load at both ends of the cut, and establish stress intensity factor of fracture tip or relational expression between mechanical energy release rate and fracture extension length to analyze the subcritical propagation rate of fractures. This method is widely used to test fracture propagation rate of crystal materials and glass. The double-torsion sample method, also known as load-relaxation method at constant displacement, is mainly used to test the subcritical propagation rate of fractures in ceramic materials and rocks. With this method, it is required to machine the sample into a rectangular thin plate (180 mm×60 mm×4 mm in size, with polished surface), and mechanically make an artificial fracture along the center of one side of the sample (a cut of 10 mm long and 1 mm wide) and a guide groove (1 mm wide and as high as ⅓ of the width) throughout the long axis. A four-point bending load is applied at the fracture breakpoint to promote the fracture propagation, and then the fracture propagation rate is calculated with relevant formulas. The advantages of the above two methods lie in that the post-processing of experimental data is relatively simple, a rate curve can be obtained from a sample, and the data continuity is sound. However, their limitations are also obvious: (1) The sample preparation process of the two test methods is complicated and requires artificial fracture prefabrication, but cannot completely reflect the subcritical propagation process of natural fractures inside the samples; (2) Due to the special configuration of samples, neither of these two test methods can apply effective stress (confining pressure) in the test, greatly restricting the study on subcritical fracture propagation under high effective stress.

In the process of drilling, completion and hydraulic fracturing of oil and gas production, the subcritical propagation of fractures in deep formation usually takes place under the action of high effective stress. Therefore, in view of the shortcomings of the existing experimental test method for subcritical propagation rate of rock fractures, the present invention proposes an experimental test method for subcritical propagation rate of rock fractures based on triaxial stress-strain curve, so as to realize the experimental test for the subcritical propagation rate of rock fractures under high effective stress.

SUMMARY OF THE INVENTION

The technical solution of the present invention is as follows:

An experimental test method for subcritical propagation rate of rock fractures based on triaxial stress-strain curve, comprising the following steps:

Step 1: Prepare the test sample for the experiment: drill and cut the core used in the experiment and then dry the core at set temperature to constant weight;

Step 2: Put the dried core into the GCTS triaxial rock mechanics test system, apply constant radial confining pressure to the core, and then apply axial stress in the axial direction until the core is macroscopically damaged; meanwhile, record the experimental parameters of axial stress, strain and corresponding loading time of the core throughout the loading test;

Step 3: Draw the stress-strain relation curve of the test core according to the detection data points of axial stress and axial strain during the experimental loading process, and divide the curve into the following five stages:

Stage I is defined as compaction stage at which the fracture in the core is closed under stress, but for the dense core, this stage is often not obvious and difficult to distinguish;

Stage II is defined as elastic deformation stage at which the pores between particles in the core are compressed and deformed but the fractures do not propagate, the core is deformed uniformly, and the stress-strain curve is approximately straight;

Stage III is defined as stable fracture propagation stage of which the starting point corresponds to the initiation stress $\sigma_{ci}$ of the test core; when the applied stress is greater than the initiation stress, the small fractures in the core will slowly propagate with the increase of load, causing the whole rock to expand volumetrically; with further propagation, the external micro-fractures in the core begin to arrange in a direction gradually; in this stage, the stress-strain curve is also approximately straight;

Stage IV is defined as unstable fracture propagation stage of which the stress at the starting point is called fracture damage stress $\sigma_{cd}$; from the starting point, the fracture propagation rate increases rapidly, and the state of the core changes from volume compression to volume expansion; the fractures will unstably propagate and begin to join together, eventually making the sample completely damaged;

Stage V is defined as post-peak deformation stage of which the starting point of this stage is the peak stress of the curve, that is, the uniaxial/triaxial compressive strength $\sigma_c$ of the core;

Step 4: In the stress-strain curve of the test core, the starting and ending time of Stage III, i.e., the subcritical propagation stage of fractures inside the core, correspond to the initiation stress $\sigma_{ci}$ and damage stress $\sigma_{cd}$, respectively; when the applied axial stress is greater than the fracture initiation stress $\sigma_{ci}$, the fractures will continue to propagate slowly, but when the applied stress disappears, the fractures will stop propagating and will not damage the core macroscopically; when the applied axial stress is greater than the fracture damage stress $\alpha_{cd}$, the fractures will enter the rapid unstable propagation stage, i.e., Stage IV;

Calculate the initiation stress $\sigma_{ci}$ and damage stress $\sigma_{cd}$ of the fracture based on the stress-strain curve of the test core, and work out the starting and ending time $T_{ci}$ and $T_{cd}$ of the subcritical fracture propagation corresponding to the initiation stress $\sigma_{ci}$ and damage stress $\sigma_{cd}$ of the fracture according to the relationship between the axial stress and the time obtained by monitoring the test process; further calculate the fracture lengths $C_{ci}$ and $C_{cd}$ corresponding to the initiation stress $\sigma_{ci}$ and damage stress $\sigma_{cd}$ of the fracture according to the theory of fracture mechanics; then calculate subcritical propagation rate of Stage III, i.e., the subcritical fracture propagation stage of the test core according to Formula (1):

$$u = \frac{C_{ci} - C_{cd}}{T_{ci} - T_{cd}}. \tag{1}$$

Where, u—subcritical propagation rate of the fracture in the test core in the subcritical propagation stage, in m/s;

$T_{ci}$ and $T_{cd}$—Starting and ending time of the subcritical fracture propagation stage in the loading process of the test core, in s;

$C_{ci}$ and $C_{cd}$—Fracture length at the starting and ending time of the subcritical fracture propagation stage of the test core, in m.

Further, Step 5: in the stress-strain curve of the test core, fractures do not propagate and are usually in a compressed state before the subcritical fracture propagation stage (Stage III), so the fracture volume strain of the core generally increases with the increase of axial strain; after entering the subcritical fracture propagation stage, i.e., Stage III, the existing micro fractures in the core slowly propagate as the axial stress increases, resulting in the overall volume expansion of the core, and the volume of the core fractures begins to change from compression to expansion, therefore, the fracture volume strain starts to decrease with the increase of axial strain; the axial stress corresponding to the turning point where the fracture volume strain of the test core changes from increasing to decreasing with the axial strain is the fracture initiation stress $\sigma_{ci}$ of the core.

Further, for the test core, the total volume strain $\varepsilon_v$ in the loading process is composed of elastic volume strain and fracture volume strain:

$$\varepsilon_v = \varepsilon_{ev} + \varepsilon_{fv} \tag{2}$$

Where: $\varepsilon_v$—Total volume strain of the test core in loading process, dimensionless;

$\varepsilon_{ev}$—Elastic volume strain of the test core in loading process, dimensionless;

$\varepsilon_{fv}$—Fracture volume strain of the test core in loading process, dimensionless.

At the same time, the total volume strain of the test core also satisfies the following relationship with its axial strain and radial strain:

$$\varepsilon_v = \varepsilon_1 + 2\varepsilon_3 \tag{3}$$

Where: $\varepsilon 1$ and $\varepsilon 3$—Axial strain and radial strain of the test core in loading process, dimensionless, which can be directly monitored in the stress-strain curve test of the core;

According to Hooke's law, the theoretical elastic volume strain of rock can be calculated by the following formula:

$$\varepsilon_{ev} = \frac{1 - 2v}{E}(\sigma_1 + 2\sigma_3). \tag{4}$$

Where: $\sigma_1$—Axial stress of the test core in loading process, in MPa;

$\sigma_3$—Radial stress under constant confining pressure applied by the test equipment to the core, in MPa;

E—Elastic modulus of the test core, in GPa;

v—Poisson's ratio of the test core, dimensionless;

Combined with Formulas (2) to (4), the fracture volume strain calculation formula of the test core can be obtained as follows:

$$\varepsilon_{fv} = \varepsilon_1 + 2\varepsilon_3 - \frac{1 - 2v}{E}(\sigma_1 + 2\sigma_3). \tag{5}$$

Further, Step 6: in the subcritical fracture propagation stage, i.e., Stage III, although the fracture volume of the test core begins to change from compression to expansion, the core is still under compression, and the total volume strain increases with the increase in axial strain; when the fracture enters the unstable propagation stage, i.e., Stage IV, the fracture propagation rate increases sharply, the total volume of the core changes from compression to expansion, and the total volume strain begins to decrease with the increase of axial strain; the axial stress corresponding to the turning point where the axial strain changes from increasing to decreasing with the axial strain is the damage stress $\sigma_{cd}$ of the core;

Step 7: According to the above experimental test and calculation results, with the axial strain of the core as the abscissa, draw the curves, i.e., the axial stress-axial strain curve, fracture volume strain-axial strain curve and total volume strain-axial strain curve; based on the turning point where the fracture volume strain and total volume strain first increase and then decrease with the axial strain, the fracture initiation stress $\sigma_{ci}$ and damage stress $\sigma_{cd}$ of the core at the starting and ending time of the subcritical fracture propagation stage (Stage III) can be directly determined on the stress-strain curve; furthermore, draw the axial stress-loading time curve of the test process, and determine the starting and ending time $T_{ci}$ and $T_{cd}$ of the subcritical fracture propagation stage on the basis of the initiation stress and damage stress of the core.

Further, Step 8: for the test core under both radial confining pressure and axial compression, the internal fractures are closed under compression, and the effective shear stress on the fracture surface is expressed as follows:

$$\tau_{\mathit{eff}} = \tau_n - \mu\sigma_n = \frac{1}{2}(\sigma_1 - \sigma_3)\sin 2\beta - \mu(\sigma_1\sin^2\beta + \sigma_3\cos^2\beta). \quad (6)$$

Where: $\tau_{\mathit{eff}}$—Effective shear stress of the test core on fracture surface, in MPa;

$\tau_n$ and $\sigma_n$—Shear stress and normal stress of the test core on fracture surface, in MPa;

$\mu$—Friction coefficient of fracture surface of the test core, dimensionless;

$\beta$—Inclination angle of fracture surface of the test core, in °;

The stress intensity factor of fracture tip inside the test core is:

$$K_{II} = \sqrt{\pi C}\,\tau_{\mathit{eff}} = \sqrt{\pi C}\left[\frac{1}{2}(\sigma_1 - \sigma_3)\sin 2\beta - \mu(\sigma_1\sin^2\beta + \sigma_3\cos^2\beta)\right]. \quad (7)$$

Where: $K_{II}$—Type II shear stress intensity factor of the test core at fracture tip, in MPa·m$^{0.5}$;

C—Fracture length of the test core in a certain stress state, in m;

When the stress intensity factor $K_{II}$ of the fracture tip inside the core is greater than the fracture toughness $K_{IIC}$ of the core, the core fracture enters the unstable propagation stage (Stage IV); at the same time, as there is more than one fracture in the test core, the inclination angle of the fracture that preferentially enters the unstable propagation stage usually satisfies the following formula:

$$\tan 2\beta = \frac{1}{\mu}. \quad (8)$$

When the stress intensity factor $K_{II}$ of the fracture tip inside the core is just equal to the fracture toughness $K_{IIC}$, that is, the core fracture is just at the critical point between the subcritical fracture propagation stage (Stage III) and the unstable propagation stage (Stage IV), the axial stress on the core at this moment is just equal to its damage stress; the following formula can be obtained by combining Formula (6) to (8):

$$C_{cd} = \frac{1}{\pi}\left[\frac{2K_{IIC}(\sqrt{\mu^2+1}+\mu)}{\sigma_{cd}-(\sqrt{\mu^2+1}+\mu)^2\sigma_3}\right]^2. \quad (9)$$

After obtaining the relevant parameters of the damage stress of the test core, the fracture length $C_{cd}$ of the test core at the ending time of the subcritical fracture propagation can be obtained according to Formula (9);

Step 9: For the test core without subcritical fracture propagation but only with micro fractures developed inside, at the starting time of the subcritical fracture propagation stage, the fractures inside the core are usually only a few microns to tens of microns long, which is far less than the fracture length at the ending time of the subcritical propagation stage, so normally, the initial fracture length $C_{ci}$ can be approximately taken as zero;

Step 10: According to the above experimental test and calculation results, obtain the fracture length $C_{ci}$ and $C_{cd}$ and the corresponding time $T_{ci}$ and $T_{cd}$ at the starting and ending time of the subcritical fracture propagation of the test core, and calculate the subcritical fracture expansion rate of the core in the subcritical fracture expansion stage according to Formula (1).

Further, the rock used as the experimental test sample is cylindrical, and the core is cut out with a diameter of 2.5 cm and a length of 5.0 cm; it is required that there are no visible fractures in the core and the drying temperature of the core is set at 60° C.

The present invention has the following beneficial effects:

(1) The method disclosed in the present invention adopts a small core plunger sample for testing. It only needs to drill and cut the core, without prefabricated artificial fractures and surface polishing. Compared with the double-torsion sample method commonly used in the prior art, the core preparation process is greatly simplified, and the success rate of sample preparation and test is enhanced significantly;

(2) Compared with the double-torsion sample method, the method disclosed in the present invention does not require artificial fracture prefabrication but can reflect the subcritical propagation process of the original natural fractures in the core;

(3) The present invention innovatively deduces the calculation formula of the subcritical fracture propagation rate of the core in the subcritical propagation stage, which greatly simplifies the experimental data acquisition and can obtain more accurate results;

(4) The double-torsion sample method can only test the subcritical propagation rate of the rock under point load, but cannot test the subcritical propagation rate of the fracture under high applied effective stress; it is difficult to reflect the influence of the effective formation stress on the subcritical propagation of the fracture; the method disclosed in the present invention can simulate the high effective stress of deep reservoir to test the subcritical fracture propagation rate of the core.

DETAILED DESCRIPTION OF THE PREFERRED EMBODIMENTS

The present invention is further described with reference to the drawings and embodiments.

An experimental test method for subcritical propagation rate of rock fractures based on triaxial stress-strain curve, comprising the following steps:

Step 1: Prepare the test sample for the experiment according to the rock sample preparation method stated in SYT5358-2010: drill and cut a core with a diameter of about 2.5 cm and a length of about 5.0 cm, without visible fractures, and dry the core the core at 60° C. to constant weight.

Step 2: Put the dried core into the GCTS triaxial rock mechanics test system, apply constant confining pressure (radial stress) to the core, and then apply axial stress in the axial direction until the core is macroscopically damaged; meanwhile, record the experimental parameters of axial stress, strain and corresponding loading time of the core throughout the loading test.

Step 3: Draw the stress-strain relation curve of the test core according to the detection data points of axial stress and axial strain during the experimental loading process, and generally divide the curve into the following five stages: Stage I is defined as compaction stage at which the fracture in the core is closed under stress, but for the dense core, this stage is often not obvious and difficult to distinguish; Stage II is defined as elastic deformation stage at which the pores between particles in the core are compressed and deformed but the fractures do not propagate, the core is deformed uniformly, and the stress-strain curve is approximately straight; Stage III is defined as stable fracture propagation stage of which the starting point corresponds to the initiation stress $\sigma_{ci}$ of the test core; when the applied stress is greater than the initiation stress, the small fractures in the core will slowly propagate with the increase of load, causing the whole rock to expand volumetrically; with further propagation, the external micro-fractures in the core begin to arrange in a direction gradually; in this stage, the stress-strain curve is also approximately straight; Stage IV is defined as unstable fracture propagation stage of which the stress at the starting point is called fracture damage stress $\sigma_{cd}$; from the starting point, the fracture propagation rate increases rapidly, and the state of the core changes from volume compression to volume expansion; the fractures will unstably propagate and begin to join together, eventually making the sample completely damaged; Stage V is defined as post-peak deformation stage of which the starting point of this stage is the peak stress of the curve, that is, the uniaxial/triaxial compressive strength a of the core.

Step 4: In the stress-strain curve of the test core, the starting and ending time of Stage III, i.e., the subcritical propagation stage of fractures inside the core, correspond to the initiation stress $\sigma_{ci}$ and damage stress $\sigma_{cd}$, respectively; when the applied axial stress is greater than the fracture initiation stress $\sigma_{ci}$, the fractures will continue to propagate slowly, but when the applied stress disappears, the fractures will stop propagating and will not damage the core macroscopically; when the applied axial stress is greater than the fracture damage stress $\sigma_{cd}$, the fractures will enter the rapid unstable propagation stage (Stage IV).

Calculate the initiation stress $\sigma_{ci}$ and damage stress $\sigma_{cd}$ of the fracture based on the stress-strain curve of the test core, and work out the starting and ending time $T_{ci}$ and $T_{cd}$ of the subcritical fracture propagation corresponding to the initiation stress $\sigma_{ci}$ and damage stress $\sigma_{cd}$ of the fracture according to the relationship between the axial stress and the time obtained by monitoring the test process; further calculate the fracture lengths $C_{ci}$ and $C_{cd}$ corresponding to the initiation stress $\sigma_{ci}$ and damage stress $\sigma_{cd}$ of the fracture according to the theory of fracture mechanics; then calculate subcritical propagation rate of the subcritical fracture propagation stage (Stage III) of the test core according to Formula (1):

$$u = \frac{C_{ci} - C_{cd}}{T_{ci} - T_{cd}}. \tag{1}$$

Where, u—subcritical propagation rate of the fracture in the test core in the subcritical propagation stage, in m/s;

$T_{ci}$ and $T_{cd}$—Starting and ending time of the subcritical fracture propagation stage in the loading process of the test core, in s;

$C_{ci}$ and $C_{cd}$—Fracture length at the starting and ending time of the subcritical fracture propagation stage of the test core, in m.

Step 5: in the stress-strain curve of the test core, fractures do not propagate and are usually in a compressed state before the subcritical fracture propagation stage (Stage III), so the fracture volume strain of the core generally increases with the increase of axial strain; after entering the subcritical fracture propagation stage (Stage III), the existing micro fractures in the core slowly propagate as the axial stress increases, resulting in the overall volume expansion of the core, and the volume of the core fractures begins to change from compression to expansion, therefore, the fracture volume strain starts to decrease with the increase of axial strain; the axial stress corresponding to the turning point where the fracture volume strain of the test core changes from increasing to decreasing with the axial strain is the fracture initiation stress $\sigma_{ci}$ of the core;

For the test core, the total volume strain $\varepsilon_v$ in the loading process is composed of elastic volume strain and fracture volume strain:

$$\varepsilon_v = \varepsilon_{ev} + \varepsilon_{fv} \tag{2}$$

Where: $\varepsilon_v$—Total volume strain of the test core in loading process, dimensionless;

$\varepsilon_{ev}$—Elastic volume strain of the test core in loading process, dimensionless;

$\varepsilon_{fv}$—Fracture volume strain of the test core in loading process, dimensionless;

At the same time, the total volume strain of the test core also satisfies the following relationship with its axial strain and radial strain:

$$\varepsilon_v = \varepsilon_1 \pm 2\varepsilon_3 \tag{3}$$

Where: $\varepsilon_1$ and $\varepsilon_3$—Axial strain and radial strain of the test core in loading process, dimensionless, which can be directly monitored in the stress-strain curve test of the core;

According to Hooke's law, the theoretical elastic volume strain of rock can be calculated by the following formula:

$$\varepsilon_{ev} = \frac{1-2v}{E}(\sigma_1 + 2\sigma_3). \tag{4}$$

Where: $\sigma_1$—Axial stress of the test core in loading process, in MPa;

$\sigma_3$—Radial stress under constant confining pressure applied by the test equipment to the core, in MPa;

E—Elastic modulus of the test core, in GPa;

v—Poisson's ratio of the test core, dimensionless; Combined with Formulas (2) to (4), the fracture volume strain calculation formula of the test core can be obtained as follows:

$$\varepsilon_{fv} = \varepsilon_1 + 2\varepsilon_3 - \frac{1-2v}{E}(\sigma_1 + 2\sigma_3). \tag{5}$$

Step 6: in the subcritical fracture propagation stage (Stage III), although the fracture volume of the test core begins to change from compression to expansion, the core is still under compression, and the total volume strain increases with the increase in axial strain; when the fracture enters the unstable propagation stage (Stage IV), the fracture propagation rate increases sharply, the total volume of the core changes from compression to expansion, and the total volume strain begins to decrease with the increase of axial strain; similarly, the axial stress corresponding to the turning point where the axial strain changes from increasing to decreasing with the axial strain is the damage stress $\sigma_{cd}$ of the core.

Step 7: according to the above experimental test and calculation results, with the axial strain of the core as the abscissa, draw the curves, i.e., the axial stress-axial strain curve, fracture volume strain-axial strain curve and total volume strain-axial strain curve; based on the turning point where the fracture volume strain and total volume strain first increase and then decrease with the axial strain, the fracture initiation stress $\sigma_{ci}$ and damage stress $\sigma_{cd}$ of the core at the starting and ending time of the subcritical fracture propagation stage (Stage III) can be directly determined on the stress-strain curve; furthermore, draw the axial stress-loading time curve of the test process, and determine the starting and ending time $T_{ci}$ and $T_{cd}$ of the subcritical fracture propagation stage (Stage III) on the basis of the initiation stress and damage stress of the core;

Step 8: for the test core under both radial (confining pressure) and axial compression, the internal fractures are closed under compression, and the effective shear stress on the fracture surface is expressed as follows:

$$\tau_{eff} = \tau_n - \mu\sigma_n = \frac{1}{2}(\sigma_1 - \sigma_3)\sin2\beta - \mu(\sigma_1\sin^2\beta + \sigma_3\cos^2\beta). \quad (6)$$

Where: $T_{eff}$—Effective shear stress of the test core on fracture surface, in MPa;

$\tau_n$ and $\sigma_n$—Shear stress and normal stress of the test core on fracture surface, in MPa;

μ—Friction coefficient of fracture surface of the test core, dimensionless;

β—Inclination angle of fracture surface of the test core, in °.

The stress intensity factor of fracture tip inside the test core is:

$$K_{II} = \sqrt{\pi C}\, \tau_{eff} = \sqrt{\pi C}\left[\frac{1}{2}(\sigma_1 - \sigma_3)\sin2\beta - \mu(\sigma_1\sin^2\beta + \sigma_3\cos^2\beta)\right]. \quad (7)$$

Where: $K_{II}$—Type II shear stress intensity factor of the test core at fracture tip, in MPa·m$^{0.5}$;

C—Fracture length of the test core in a certain stress state, in m.

When the stress intensity factor $K_{II}$ of the fracture tip inside the core is greater than the fracture toughness $K_{IIC}$ of the core, the core fracture enters the unstable propagation stage (Stage IV); at the same time, as there is more than one fracture in the test core, the inclination angle of the fracture that preferentially enters the unstable propagation stage usually satisfies the following formula:

$$\tan2\beta = \frac{1}{\mu}. \quad (8)$$

When the stress intensity factor $K_{II}$ of the fracture tip inside the core is just equal to the fracture toughness $K_{IIC}$, that is, the core fracture is just at the critical point between the subcritical fracture propagation stage (Stage III) and the unstable propagation stage (Stage IV), the axial stress on the core at this moment is just equal to its damage stress; the following formula can be obtained by combining Formula (6) to (8):

$$C_{cd} = \frac{1}{\pi}\left[\frac{2K_{IIC}\left(\sqrt{\mu^2+1}+\mu\right)}{\sigma_{cd} - \left(\sqrt{\mu^2+1}+\mu\right)^2\sigma_3}\right]^2. \quad (9)$$

After obtaining the relevant parameters of the damage stress of the test core, the fracture length $C_{cd}$ of the test core at the ending time of the subcritical fracture propagation can be obtained according to Formula (9).

Step 9: For the test core without subcritical fracture propagation but only with micro fractures developed inside, at the starting time of the subcritical fracture propagation stage, the fractures inside the core are usually only a few microns to tens of microns long, which is far less than the fracture length at the ending time of the subcritical propagation stage, so normally, the initial fracture length $C_{ci}$ can be approximately taken as zero.

Step 10: According to the above experimental test and calculation results, obtain the fracture length ($C_{ci}$ and $C_{cd}$) and the corresponding time ($T_{ci}$ and $T_{cd}$) at the starting and ending time of the subcritical fracture propagation of the test core, and calculate the subcritical fracture expansion rate of the core in the subcritical fracture expansion stage according to Formula (1).

Embodiment

Cores was selected and taken from deep shale formation in a block in Sichuan Basin to conduct experiments based on the detailed implementation of the above steps. The specific process is described as follows.

Step 1: Select and take cores from deep shale formation in a block in Sichuan Basin, drill and prepare test cores L-1 and L-2 (Table 1) according to the rock sample preparation method stated in SYT5358-2010; the cores had no visible fractures and were dried at 60° C. to constant weight.

Step 2: Put the dried core into the GCTS triaxial rock mechanics test system, apply constant confining pressure (radial stress) of 30 MPa to the core, and apply axial stress in the axial direction after the confining pressure is stable; in order to satisfy the quasi-static loading requirement in test, the axial loading rate is only 0.005 mm/s; record the experimental parameters such as axial stress, strain and corresponding loading time of the core throughout the loading test until the core is macroscopically damaged and the loading is stopped.

Step 3: According to the data on axial stress and axial strain of the core measured in the experiment, draw the axial stress-axial strain curve (FIG. 1A and FIG. 1B) of the core with the axial strain as the abscissa, and generally divide the curve into the five stages: Stage I, compaction stage; Stage II, elastic deformation stage; Stage III, stable fracture propagation stage; Stage IV, unstable fracture propagation stage; and Stage V, post-peak deformation stage, of which Stage III (stable fracture propagation stage) is the subcritical fracture propagation stage of rock; test the subcritical propagation rate of rock fractures; the key is to clarify the parameters such as the starting and ending time of the subcritical fracture propagation stage (Stage III) of the core.

Step 4: In the stress-strain curve of the test core, the starting and ending time of the subcritical fracture propagation stage (Stage III) of the core correspond to the initiation stress $\sigma_{ci}$ and damage stress $\sigma_{cd}$; after determining the initiation stress $\sigma_{ci}$ and damage stress $\sigma_{cd}$ of cores L-1 and L-2, obtain the values of starting and ending time $T_{ci}$ and $T_{cd}$ of the subcritical fracture propagation stage according to the relation curves of axial stress and loading time of cores L-1 and L-2; further calculate the fracture lengths $C_{ci}$ and $C_{cd}$ corresponding to the initiation stress $\sigma_{ci}$ and damage stress $\sigma_{cd}$ of the fracture according to the theory of fracture mechanics; then calculate subcritical propagation rate of Stage III, i.e., the subcritical fracture propagation stage of the test core according to Formula (1):

$$u = \frac{C_{ci} - C_{cd}}{T_{ci} - T_{cd}}. \tag{1}$$

Step 5: for the test cores L-1 and L-2, the total volume strain $\varepsilon_v$ in the loading process is composed of elastic volume strain and fracture volume strain:

$$\varepsilon_v = \varepsilon_{ev} + \varepsilon_{fv} \tag{2}$$

At the same time, the total volume strain of the test core also satisfies the following relationship with its axial strain and radial strain:

$$\varepsilon_v = \varepsilon_1 + 2\varepsilon_3 \tag{3}$$

According to Hooke's law, the theoretical elastic volume strain of rock can be calculated by the following formula:

$$\varepsilon_{ev} = \frac{1-2v}{E}(\sigma_1 + 2\sigma_3). \tag{4}$$

In Formulas (2) to (4), the axial stress ($\sigma_1$), axial strain ($\varepsilon_1$) and radial strain ($\varepsilon_3$) of the test cores L-1 and L-2 can be monitored and recorded directly in the experimental process; the radial stress ($\sigma_3$) is a fixed value of 30 MPa applied by the instrument; the elastic modulus (E) and Poisson's ratio (v) of the cores L-1 and L-2 are determined in advance through other experiments, and their values are shown in Table 1; according to Formula (5), the fracture volume strain of the cores L-1 and L-2 at different loading time can be calculated;

$$\varepsilon_{fv} = \varepsilon_1 + 2\varepsilon_3 - \frac{1-2v}{E}(\sigma_1 + 2\sigma_3). \tag{5}$$

Figure 1A:
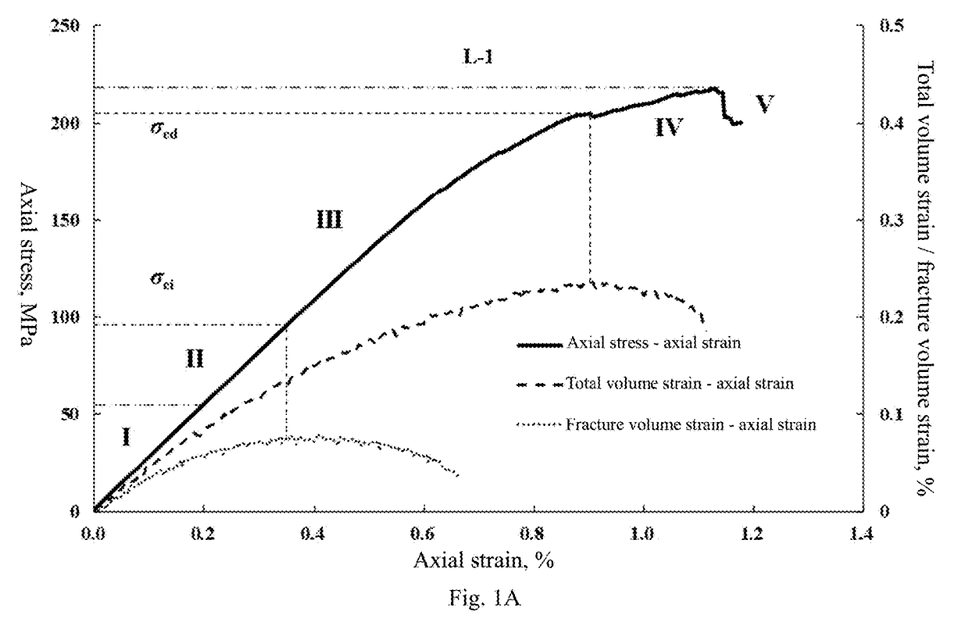
FIG. 1A and FIG. 1B show the axial stress/fracture volume strain/total volume strain-axial strain curves of the test cores L-1 and L-2 in the embodiment.
Figure 1B:
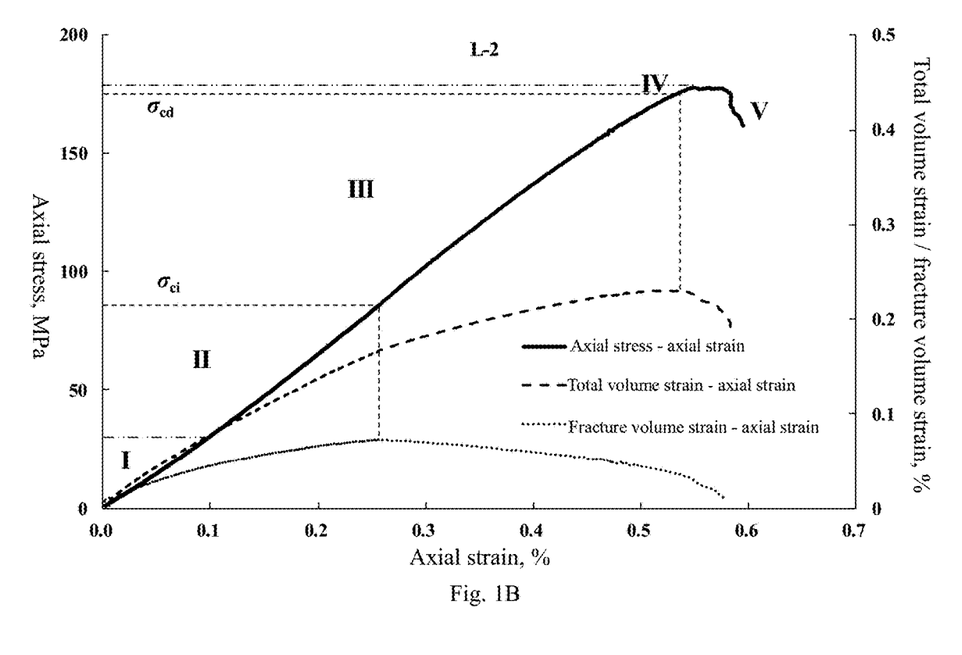

According to the calculation results, take the axial strain as the abscissa and draw the fracture volume strain-axial strain relation curve of the core in the testing process; as shown in FIG. 1A and FIG. 1B, when the axial stress corresponding to the turning point where the fracture volume strain of test cores L-1 and L-2 changes from increasing to decreasing with the axial strain is the fracture damage stress $\sigma_{ci}$ of the core; the method for obtaining values at the turning point is to first perform polynomial fitting on the fracture volume strain-axial strain relation curve, and then calculate the derivative and the extreme value to obtain the corresponding values at the turning point, that is, the turning point value is obtained by calculating the derivative and the extreme value of the curve; in this embodiment, the $\sigma_{ci}$ values of the cores L-1 and L-2 are 97 MPa and 85 MPa respectively.

TABLE 1

Basic Rock Mechanics Parameters of Test Core L-1

| Parameters | L-1 | L-2 |
| --- | --- | --- |
| Length (cm) | 5.04 | 5.02 |
| Diameter (cm) | 2.51 | 2.51 |
| Mass (g) | 68.1275 | 67.9461 |
| Fracture toughness $K_{IIC}$, MPa · m$^{0.5}$ | 1.62 | 1.58 |
| Elastic modulus E, GPa | 27.4 | 31.6 |
| Poisson's ratio v, dimensionless | 0.23 | 0.22 |
| Friction coefficient of fracture surface μ, dimensionless | 0.54 | 0.51 |
| Confining pressure (radial stress) $\sigma_3$, MPa | 30 | 30 |

Step 6: According to Formula (3) and monitoring data during experiment, calculate the total volume strain $\varepsilon_v$ of the test core in the loading process, take the axial strain as the abscissa and draw the total volume strain-axial strain relation curve of the cores L-1 and L-2 in the test process; as shown in FIG. 1A and FIG. 1B, when the axial stress corresponding to the turning point where the total volume strain of the cores L-1 and L-2 changes from increasing to decreasing with the axial strain is the damage stress $\sigma_{cd}$ of the core; the method for obtaining values at the turning point is to first perform polynomial fitting on the fracture volume strain-axial strain relation curve, and then calculate the derivative and the extreme value to obtain the corresponding values at the turning point; in this embodiment, the values of $\sigma_{cd}$ of the cores L-1 and L-2 are 206 MPa and 175 MPa.

Figure 2A:
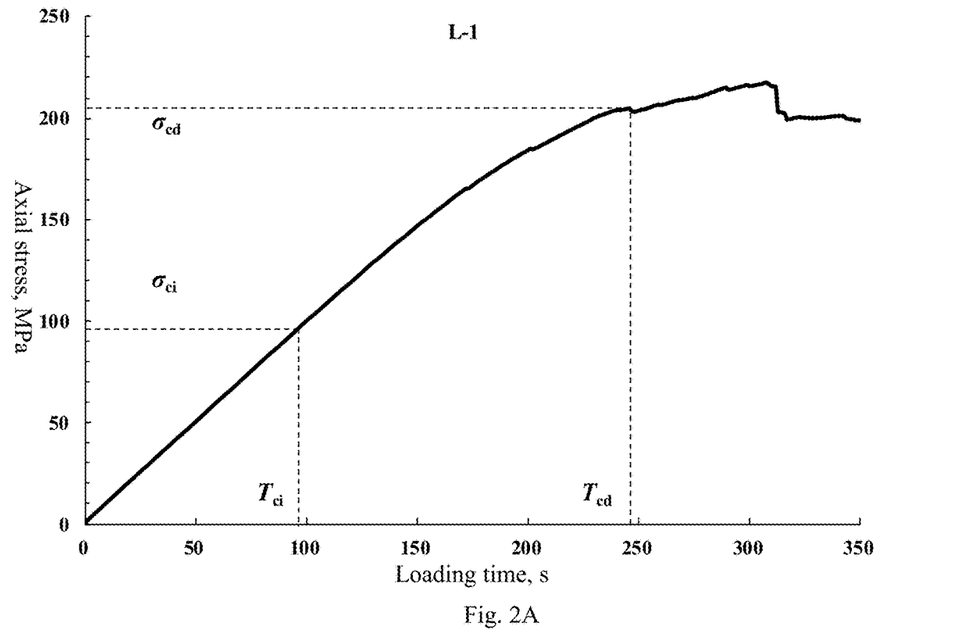
FIG. 2A and FIG. 2B show the axial stress-loading time curve of the test core.
Figure 2B:
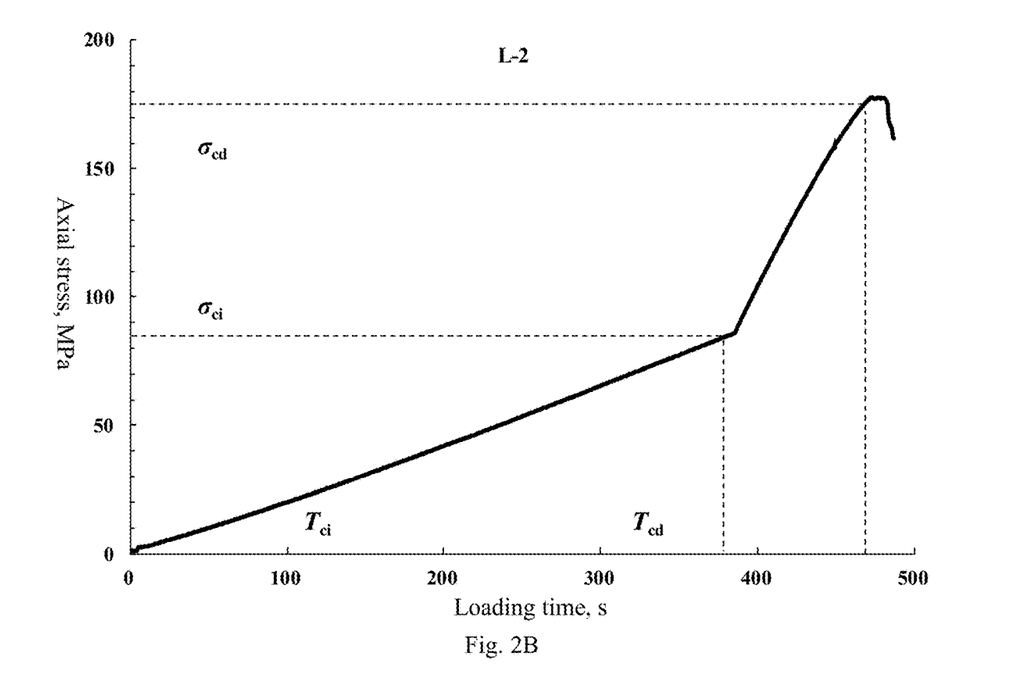

Step 7: According to the experimental monitoring data, draw the axial stress-loading time curve of the cores L-1 and L-2 in the test process (FIG. 2A and FIG. 2B); with given core fracture stress $\sigma_{ci}$ and damage stress $\sigma_{cd}$, calibrate the starting and ending time $T_{ci}$ and $T_{cd}$ of the cores L-1 and L-2 in the subcritical fracture propagation stage based on the axial stress-loading time curve as shown in FIG. 2A and FIG. 2B; in this embodiment, $T_{ci}$ and $T_{cd}$ of the cores L-1 and L-2 are taken as 96.13 s and 381.52 s, and 246.87 s and 468.75 s, respectively.

Step 8: for the test core under both radial (confining pressure) and axial compression, the internal fractures are closed under compression, and the effective shear stress on the fracture surface is expressed as follows:

$$\tau_{eff} = \tau_n - \mu\sigma_n = \frac{1}{2}(\sigma_1 - \sigma_3)\sin 2\beta - \mu(\sigma_1 \sin^2\beta + \sigma_3 \cos^2\beta). \tag{6}$$

The stress intensity factor of fracture tip inside the test core is:

$$K_{II} = \sqrt{\pi C}\,\tau_{eff} = \sqrt{\pi C}\left[\frac{1}{2}(\sigma_1 - \sigma_3)\sin 2\beta - \mu(\sigma_1 \sin^2\beta + \sigma_3 \cos^2\beta)\right]. \tag{7}$$

When the stress intensity factor $K_{II}$ of the fracture tip inside the core is greater than the fracture toughness $K_{IIC}$ of the core, the core fracture enters the unstable propagation stage (Stage IV); at the same time, as there is more than one fracture in the test core, the inclination angle of the fracture that preferentially enters the unstable propagation stage usually satisfies the following formula:

$$\tan 2\beta = \frac{1}{\mu}. \qquad (8)$$

When the stress intensity factor $K_{II}$ of the fracture tip inside the core is just equal to the fracture toughness $K_{IIC}$, that is, the core fracture is just at the critical point between the subcritical fracture propagation stage (Stage III) and the unstable propagation stage (Stage IV), the axial stress on the core at this moment is just equal to its damage stress; the following formula can be obtained by combining Formula (6) to (8):

$$C_{cd} = \frac{1}{\pi}\left[\frac{2K_{IIC}\left(\sqrt{\mu^2+1}+\mu\right)}{\sigma_{cd}-\left(\sqrt{\mu^2+1}+\mu\right)^2\sigma_3}\right]^2. \qquad (9)$$

If relevant parameters such as fracture toughness of the test cores L-1 and L-2 are known (Table 1), work out the fracture length $C_{cd}$ of the test core at the ending time of the subcritical fracture propagation stage according to Formula (9); the calculated values of $C_{cd}$ of the cores L-1 and L-2 in this embodiment are $6.34\times10^{-4}$ m and $5.28\times10^{-4}$ m, respectively.

Figure 3A:
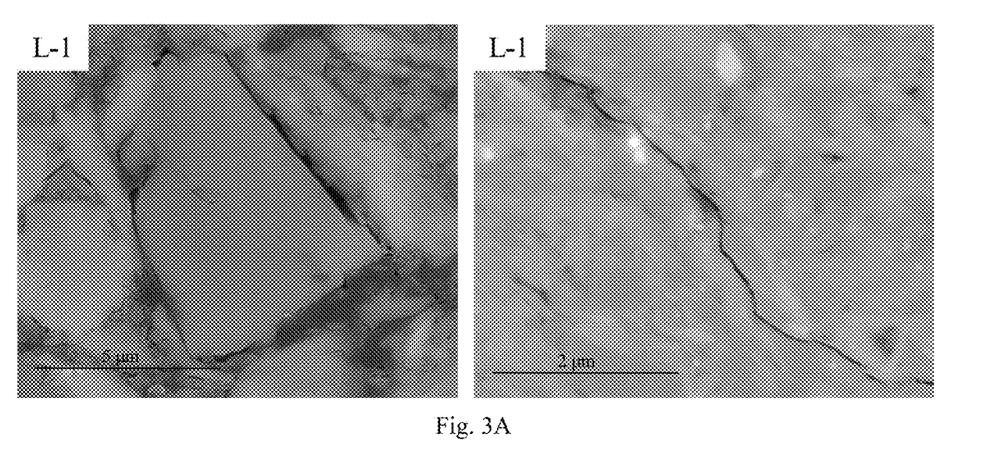
FIG. 3A and FIG. 3B show the fracture image observed by scanning electron microscope when the test core does not subcritically propagate before the experiment.
Figure 3B:
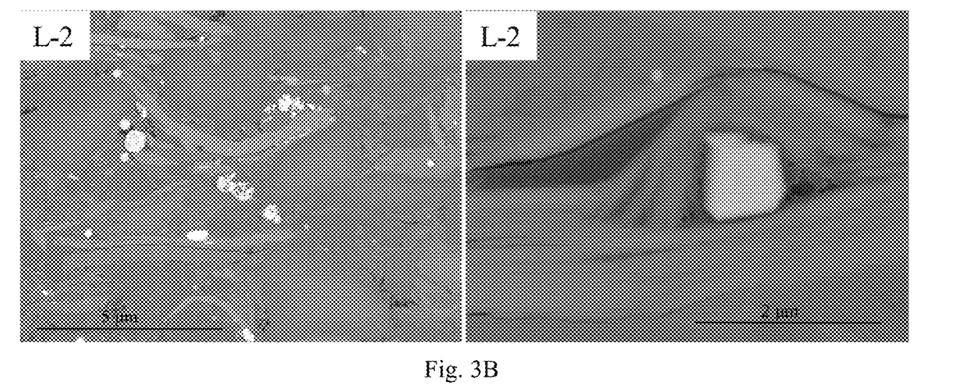

Step 9: For cores L-1 and L-2, as observed by scanning electron microscope, before the subcritical propagation of fractures in the core (as shown in FIG. 3A and FIG. 3B), there are only micro fractures with length ranging from several to tens of microns, which is far less than the fracture length $C_{cd}$ at the ending time of the subcritical fracture propagation stage of the core (less than 2% of the $C_{cd}$ value); therefore, at the starting time of the subcritical fracture propagation stage, the initial fracture length Gi of the cores L-1 and L-2 can be approximately zero, so it is taken as 0.

Step 10: According to Formula (1), calculate the subcritical fracture propagation rates of test cores L-1 and L-2 in the subcritical fracture propagation stage to be $4.21\times10^{-6}$ m and $6.05\times10^{-6}$ m, respectively; test the subcritical propagation rate of rock fractures under high effective stress (confining pressure) for the first time based on the stress-strain curve; the measured values are generally lower than the subcritical propagation rate of Devonian shale fractures measured by Swanson et al. (Swanson P L. Subcritical fracture growth and other time- and environment-dependent behavior in crustal rocks [J]. Journal of Geophysical Research: Solid Earth, 1984, 89(B6):4137-52.) through the double-torsion sample method; the main reason is that the method simulates the high effective stress conditions of the rock in the formation, and more objectively reflects the effect of effective stress on inhibiting the subcritical propagation process of shale fractures.

The above are not intended to limit the present invention in any form. Although the present invention has been disclosed as above with embodiments, it is not intended to limit the present invention. Those skilled in the art, within the scope of the technical solution of the present invention, can use the disclosed technical content to make a few changes or modify the equivalent embodiment with equivalent changes. Within the scope of the technical solution of the present invention, any simple modification, equivalent change and modification made to the above embodiments according to the technical essence of the present invention are still regarded as a part of the technical solution of the present invention.

What is claimed is:

1. An experimental test method for subcritical propagation rate of rock fractures based on triaxial stress-strain curve, comprising the following steps:
    Step 1: preparing a test sample for experiment: drilling and cutting a core used in the experiment, and then drying the core to constant weight at a set temperature;
    Step 2: putting the dried core into a GCTS triaxial rock mechanics test system, applying constant radial confining pressure to the core, and then applying axial stress in an axial direction until the core is macroscopically damaged; meanwhile, recording experimental parameters of axial stress, strain and corresponding loading time of the core throughout the loading test;
    Step 3: drawing a stress-strain curve of the test core according to detection data points of axial stress and axial strain during the experimental loading process, and dividing the curve into the following five stages:
        Stage I is defined as a compaction stage at which fractures in the core are closed under stress, but for the dense core, this stage is often not obvious and difficult to distinguish;
        Stage II is defined as an elastic deformation stage at which pores between particles in the core are compressed and deformed but the fractures do not propagate, the core is deformed uniformly, and the stress-strain curve is approximately straight;
        Stage III is defined as a stable fracture propagation stage of which a starting point corresponds to an initiation stress σci of the test core; when the applied stress is greater than the initiation stress, the small fractures in the core will slowly propagate with the increase of load, causing the whole rock to expand volumetrically; with further propagation, external micro-fractures in the core begin to arrange in a direction gradually; in this stage, the stress-strain curve is also approximately straight;
        Stage IV is defined as an unstable fracture propagation stage of which the stress at the starting point is called fracture damage stress σcd; from the starting point, the fracture propagation rate increases rapidly, and the state of the core changes from volume compression to volume expansion; the fractures will unstably propagate and begin to join together, eventually making the sample completely damaged; and
        Stage V is defined as a post-peak deformation stage of which the starting point of this stage is a peak stress of the curve, that is, the uniaxial/triaxial compressive strength σc of the core;
    Step 4: in the stress-strain curve of the test core, a starting time and a ending time of Stage III, correspond to the initiation stress σci and the damage stress σcd, respectively; when the applied axial stress is greater than the fracture initiation stress σci, the fractures will continue to propagate slowly, but when the applied stress disappears, the fractures will stop propagating and will not damage the core macroscopically; when the applied axial stress is greater than the fracture damage stress σcd, the fractures will enter the Stage IV;
    calculating the initiation stress σci and the damage stress σcd of the fracture based on the stress-strain curve of the test core, and working out the starting time Tci and the ending time Tcd of the subcritical fracture propagation corresponding to the initiation stress σci and the damage stress σcd of the fracture according to the relationship between the axial stress and the time obtained by monitoring the test process; further calculating fracture lengths Cci and Ccd corresponding to the initiation stress σci and the damage stress σcd of the fracture according to theory of fracture mechanics; then calculating subcritical propagation rate of the Stage III of the test core according to Formula (1):

$$u = \frac{C_{ci} - C_{cd}}{T_{ci} - T_{cd}}; \tag{1}$$

where, u—the subcritical propagation rate of the fracture in the test core in the subcritical propagation stage, in m/s;
Tci and Tcd—the starting time and the ending time of the subcritical fracture propagation stage in the loading process of the test core, in s;
Cci and Ccd—the fracture lengths at the starting time and the ending time of the subcritical fracture propagation stage of the test core, in m;
Step 5: in the stress-strain curve of the test core, the fractures do not propagate and are usually in a compressed state before the Stage III so the fracture volume strain of the core generally increases with the increase of axial strain; after entering the Stage III, the existing micro fractures in the core slowly propagate as the axial stress increases, resulting in the overall volume expansion of the core, and the volume of the core fractures begins to change from compression to expansion, therefore, the fracture volume strain starts to decrease with the increase of axial strain; the axial stress corresponding to the turning point where the fracture volume strain of the test core changes from increasing to decreasing with the axial strain is the fracture initiation stress $\sigma_{ci}$ of the core;
Wherein, for the test core, the total volume strain EV in the loading process is composed of an elastic volume strain and a fracture volume strain:

$$\varepsilon_v = \varepsilon_{ev} + \varepsilon_{fv} \tag{2};$$

where: εV—the total volume strain of the test core in loading process, dimensionless;
εev—the elastic volume strain of the test core in loading process, dimensionless;
εfv—the fracture volume strain of the test core in loading process, dimensionless;
the total volume strain of the test core satisfies the following relationship with its axial strain and radial strain:

$$\varepsilon_v = \varepsilon_1 + 2\varepsilon_3 \tag{3}$$

where: ε1 and ε3—an axial strain and a radial strain of the test core in loading process, dimensionless, which is directly monitored in the stress-strain curve test of the core;
according to Hooke's law, the theoretical elastic volume strain of rock is calculated by the following formula:

$$\varepsilon_{ev} = \frac{1-2v}{E}(\sigma_1 + 2\sigma_3); \tag{4}$$

where: σ1—the axial stress of the test core in loading process, in MPa;

σ3—the radial stress under constant confining pressure applied by the test equipment to the core, in MPa;
E—the elastic modulus of the test core, in GPa;
v—a Poisson's ratio of the test core, dimensionless;
combined with Formulas (2) to (4), the fracture volume strain calculation formula of the test core is obtained as follows:

$$\varepsilon_{fv} = \varepsilon_1 + 2\varepsilon_3 - \frac{1-2v}{E}(\sigma_1 + 2\sigma_3); \tag{5}$$

according to the calculation results, taking the axial strain as the abscissa and drawing the fracture volume strain-axial strain curve of the core in the testing process.

2. The experimental test method for subcritical propagation rate of rock fractures based on triaxial stress-strain curve according to claim 1, further comprising:
Step 6: in the Stage III, although the fracture volume of the test core begins to change from compression to expansion, the core is still under compression, and the total volume strain increases with the increase in axial strain; when the fracture enters the Stage IV, the fracture propagation rate increases sharply, the total volume of the core changes from compression to expansion, and the total volume strain begins to decrease with the increase of axial strain; the axial stress corresponding to the turning point where the axial strain changes from increasing to decreasing with the axial strain is the damage stress $\sigma_{cd}$ of the core; and
Step 7: according to the above experimental test and calculation results, with the axial strain of the core as the abscissa, drawing the axial stress-axial strain curve, a fracture volume strain-axial strain curve, and a total volume strain-axial strain curve; based on a turning point where the fracture volume strain and the total volume strain first increase and then decrease with the axial strain, the fracture initiation stress $\sigma_{ci}$ and the damage stress $\sigma_{cd}$ of the core at the starting time and the ending time of the Stage III is directly determined on the stress-strain curve; drawing the axial stress-loading time curve of the test process, and determining the starting time $T_{ci}$ and the ending time $T_{cd}$ of the subcritical fracture propagation stage on the basis of the initiation stress and damage stress of the core.

3. The experimental test method for subcritical propagation rate of rock fractures based on triaxial stress-strain curve according to claim 2, further comprising:
Step 8: for the test core under both radial confining pressure and axial compression, the internal fractures are closed under compression, and the effective shear stress on the fracture surface is expressed as follows:

$$\tau_{\mathit{eff}} = \tau_n - \mu\sigma_n = \frac{1}{2}(\sigma_1 - \sigma_3)\sin 2\beta - \mu(\sigma_1\sin^2\beta + \sigma_3\cos^2\beta); \tag{6}$$

where: τeff—an effective shear stress of the test core on fracture surface, in MPa;
τn and σn—a shear stress and a normal stress of the test core on fracture surface, in MPa;
μ—a friction coefficient of fracture surface of the test core, dimensionless;
β—an inclination angle of fracture surface of the test core, in °;

the stress intensity factor of fracture tip inside the test core is:

$$K_{II} = \sqrt{\pi C}\, \tau_{eff} = \sqrt{\pi C}\left[\frac{1}{2}(\sigma_1 - \sigma_3)\sin 2\beta - \mu(\sigma_1 \sin^2\beta + \sigma_3 \cos^2\beta)\right]; \quad (7)$$

where: $K_{II}$—a type II shear stress intensity factor of the test core at fracture tip, in MPa·m$^{0.5}$;

C—the fracture length of the test core in a certain stress state, in m;

when the stress intensity factor $K_{II}$ of the fracture tip inside the core is greater than the fracture toughness $K_{IIC}$ of the core, the core fracture enters the Stage IV; as there is more than one fracture in the test core, the inclination angle of the fracture that preferentially enters the unstable propagation stage usually satisfies the following formula:

$$\tan 2\beta = \frac{1}{\mu}; \quad (8)$$

when the stress intensity factor $K_{II}$ of the fracture tip inside the core is just equal to the fracture toughness $K_{IIC}$, and the core fracture is just at a critical point between the Stage III and the Stage IV, the axial stress on the core at this moment is just equal to its damage stress; the following formula is obtained by combining Formulas (6) to (8):

$$C_{cd} = \frac{1}{\pi}\left[\frac{2K_{IIC}\left(\sqrt{\mu^2+1}+\mu\right)}{\sigma_{cd}-\left(\sqrt{\mu^2+1}+\mu\right)^2 \sigma_3}\right]^2; \quad (9)$$

after obtaining the relevant parameters of the damage stress of the test core, the fracture length Ccd of the test core at the ending time of the subcritical fracture propagation is obtained according to Formula (9);

Step 9: for the test core without subcritical fracture propagation but only with micro fractures developed inside, at the starting time of the subcritical fracture propagation stage, the fractures inside the core are usually only a few microns to tens of microns long, which is far less than the fracture length at the ending time of the subcritical propagation stage, so the initial fracture length Cci is approximately taken as zero; and Step 10: according to the above experimental test and calculation results, obtaining the fracture lengths Cci and Ccd and the corresponding time Tci and Tcd at the starting time and the ending time of the subcritical fracture propagation of the test core, and calculating the subcritical fracture expansion rate of the core in the subcritical fracture expansion stage according to Formula (1).

4. The experimental test method for subcritical propagation rate of rock fractures based on triaxial stress-strain curve according to claim 1, wherein the rock used as the experimental test sample is cylindrical, and the core is cut out with a diameter of 2.5 cm and a length of 5.0 cm; it is required that there are no visible fractures in the core and the drying temperature of the core is set at 60° C.

* * * * *